United States Patent [19]
Hardtmann

[11] 3,978,059
[45] Aug. 31, 1976

[54] CYCLIC SUBSTITUTED TRICYCLIC QUINAZOLINONES

[75] Inventor: Goetz E. Hardtmann, Florham Park, N.J.

[73] Assignee: Sandoz, Inc., E. Hanover, N.J.

[22] Filed: Nov. 6, 1972

[21] Appl. No.: 304,109

[52] U.S. Cl. .................. 260/256.5 R; 260/244 A; 260/256.4 F; 424/251
[51] Int. Cl.² ........................................ C07D 487/04
[58] Field of Search .... 260/293.59, 251 A, 256.4 F, 260/256.5 R

[56] References Cited
UNITED STATES PATENTS

| | | | |
|---|---|---|---|
| 3,309,369 | 3/1967 | Schindler | 260/256.4 |
| 3,313,815 | 4/1967 | Wolfe et al. | 260/256.4 |
| 3,379,733 | 4/1968 | Houlihan | 260/326.1 |
| 3,470,180 | 9/1969 | Houlihan | 260/251 |
| 3,600,390 | 8/1971 | Sherlock | 260/256.4 |

FOREIGN PATENTS OR APPLICATIONS 2,025,248  12/1970  Germany .................. 260/251 A

*Primary Examiner*—G. Thomas Todd
*Attorney, Agent, or Firm*—Gerald D. Sharkin; Richard E. Vila

[57] ABSTRACT

The compounds are biologically active tricyclic quinazolinones of the class of imidazo[2,1-b]quinazolin-5-ones, pyrimido[2,1-b]quinazolin-6-ones and diazepino[2,1-b]quinazolin-7-ones substituted by a thienyl or furyl group, e.g., 10-(2-thienylmethyl)-2,3-dihydro-imidazo[2,1-b]quinazolin-5(10)-one, and useful, for example, as broncho-dilator agents. Processes for preparation of said compounds include the reaction of a N-carboxy anthranilic anhydride (an isatoic anhydride) with a cyclic pseudothiourea such as 2-organomercapto-4,5-dihydroimidazole or 2-organomercapto-3,4,5,6-tetrahydropyrimidine.

7 Claims, No Drawings

CYCLIC SUBSTITUTED TRICYCLIC QUINAZOLINONES

The present invention relates to heterocyclic substituted tricyclic compounds which are quinazolinones, and to their preparation. The invention also relates to pharmaceutical methods and compositions for utilization of the compounds based on their biological activity.

The compounds of the invention may be represented by the structural formula I:

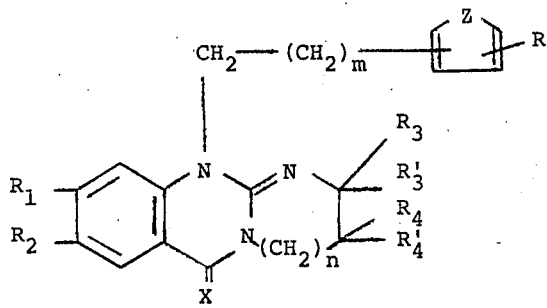

wherein
each of $R_1$ and $R_2$ is, independently, hydrogen, halo of atomic weight not greater than 36 or lower alkyl of 1 to 3 carbon atoms, or both are lower alkoxy of 1 to 6 carbon atoms; or one is hydrogen and the other bromo or lower alkoxy of 1 to 2 carbon atoms,
$n$ is 0, 1 or 2,
$m$ is 0, 1 or 2,
Z is oxygen or sulfur,
X is oxygen or sulfur,
R is hydrogen, halo of atomic weight of 18 to 36, i.e., fluoro or chloro, or alkyl of 1 to 4 carbon atoms, and
each of $R_3$, $R_3'$, $R_4$ and $R_4'$ is hydrogen or alkyl of 1 to 3 carbon atoms provided that no more than 3 of $R_3$, $R_3'$, $R_4$ and $R_4'$ are alkyl,
or a pharmaceutically acceptable acid addition salt thereof.

One method of preparation of the Compounds I in which X is oxygen involves reaction in a Step A of a compound of the formula II:

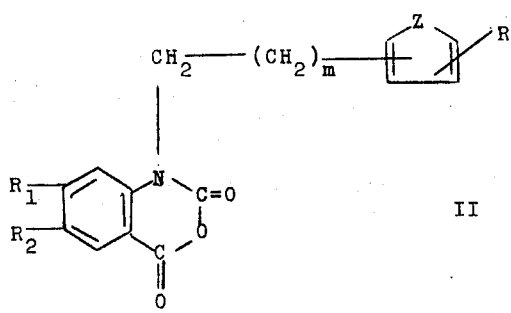

wherein R, $R_1$, $R_2$, Z and m are as defined, with a compound of formula III:

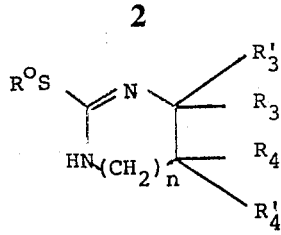

wherein $n$, $R_3$, $R_3'$, $R_4$ and $R_4'$ are as defined and $R°$ is lower alkyl or benzyl.

The preparation of compounds I by the reaction of Step A can be carried out at temperatures in the range of 20° to 160°C., more usually 20° to 140°C., preferably 80° to 120°C. The reaction is conveniently carried out in an organic solvent of conventional type providing an inert reaction medium. Cyclic ethers and aromatic solvents suitable for use at reflux temperatures represent the preferred solvents, particularly dioxane and toluene. The reaction is preferably carried out in the presence of a base, e.g., sodium hydroxide or sodium carbonate; and if the compound III is employed directly in acid addition salt form then it is desirable to employ an amount of base somewhat greater than the amount necessary to neutralize the acid. In general, the reaction product of formula I may be recovered from the reaction of Step A by working up by conventional procedures.

The compounds of the formula I in which X is oxygen may be also prepared in a Step B reaction by reacting a compound of the formula IV:

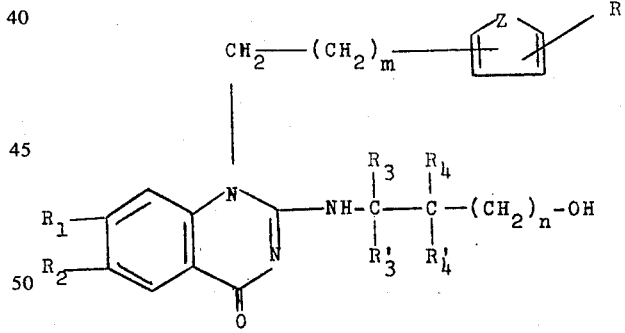

IV in which $R_1$, $R_2$, $R_3$, $R_3'$, $R_4$, $R_4'$, Z and $m$ are as above defined, with a cyclizing agent, and treating the reaction product with an acid binding agent.

The preparation of compounds I from compounds IV involves a cyclization of known type carried out by treating a compound IV with a reagent suitable for such type of cyclization, for example, a phosphorus halide or thionyl halide in which the halide has an atomic weight of from 35 to 80, i.e., the chloride or bromide, more preferably the chloride. The preferred reagent is thionyl chloride. The reaction with the cyclizing reagent may be carried out in absence of a solvent or in the presence of inert solvents of known type, e.g., the halogen-containing hydrocarbons such as methylene chloride and chloroform, and the aromatic solvents such as benzene and pyridine. An excess of the cyclizing agent may, however, where appropriate, be employed to provide a solvent. The treatment with an acid-binding agent, e.g., an inorganic base or tertiary amine, is preferably effected after removal of any remaining cyclizing reagent. The reaction product of formula I may be isolated from the Step B reaction mixture by working up by established procedures.

The compounds of the formula I in which X is sulfur may be prepared in by Step C from the corresponding compounds of the formula I in which X is oxygen by known reaction procedures for converting a cyclic ketone function to a cyclic thione function, for example, by reacting the ketone with phosphorous pentasulfide in the presence of an inert organic solvent of conventional type. Said reaction is preferably effected at a temperature of from about 70° to 180°C., more preferably from 100° to 130°C. Suitable solvents include pyridine, toluene and xylene of which pyridine is most preferred. Reaction times may vary for example from 1 to 50 hours, more typically from 10 to 30 hours. The reaction product of the formula I in which X is sulfur may be isolated from the reaction mixture of Step C by working up by conventional procedures.

The compounds of the formula II are novel and may be prepared by reacting a compound of the formula V:

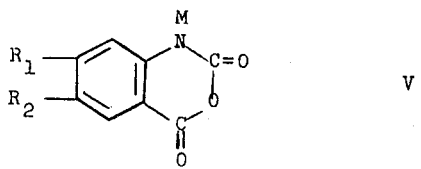

in which $R_1$ and $R_2$ are as defined and M is hydrogen or an alkali metal, with a compound of the formula VI:

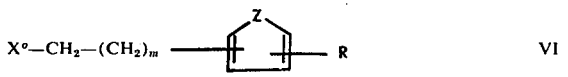

in which R, Z and $m$ are as defined with $X°$ is halo, e.g. chloro or bromo.

The preparation of compounds II from compounds V and VI may be carried out at temperatures of from 0° to 100°C., preferably 20° to 50°C. The reaction is conveniently effected in an inert organic solvent which may be of conventional type, e.g., dimethylacetamide. The reaction is preferably effected with a compound V in which M is an alkali metal and such compounds are prepared in a conventional manner by reacting a compound in which M is hydrogen with a strong base such as an alkali metal hydride, e.g., sodium hydride. If the compound V in which M is hydrogen is employed the reaction is carried out in the pressure of a strong base, e.g., an alkali metal alkoxide or hydroxide.

The compounds of formula V and VI are either known or may be prepared from known materials by established procedures. The compounds of the formula IV are also novel and may be prepared from known materials by procedures known for preparing the known corresponding N-alkyl compounds.

The preferred compounds of the invention are those having one or more of the following significances: 1) the thienyl or furyl group attached at its 2-position to the alkylene moiety; 2) Z equals sulfur; 3) R equals hydrogen; 4) $n$ equals O, 5) X being oxygen; 6) $m$ equals O; 7) $R_1$ and $R_2$ each being hydrogen; and 8) each of $R_3$, $R_3'$, $R_4$ and $R_4'$ being hydrogen, the preferred compound being 10-(2-thienylmethyl)-2,3-dihydro-imidazo[2,1-b]quinazolin-5(10H)-one.

Also within the scope of the compounds of formula I of the invention are pharmaceutically acceptable salts not materially depreciating the pharmacological effect of the compounds. Such salts include the acid addition salts of known type, e.g., the hydrochloride. The acid addition salts may be produced from the corresponding free bases by conventional procedures. Conversely, the free bases may be obtained from the salts by procedures known in the art.

The compounds of formula I of the invention are useful because they possess biological activity. In particular, the compounds of the formula I are useful as bronchodilator agents as indicated by measuring bronchial resistance on intravenous administration (0.1 – 5 mgs./kgs.) in the anesthetized guinea pig and according to the test of Knozett and Rossler, Arch. Exp. Path. and Pharmak. 195:71 (1940); and by observing the respiratory status on oral administration (0.5 – 100 mgs./kgs.) to the unanesthetized guinea pig exposed to aerosolized histamine dihydrochloride according to a modification of the method of Van Arman et al., J. Pharm. Pharmacol. Exptl. Therap. 133:90–97, 1961; and in vitro by observing the effect (0.1 – 30 micrograms/ml.) on strips of guinea pig trachea according to the method of Constantine, J. Pharm. Pharmacol. 17: 384–385, 1960. For such use and depending upon known variables satisfactory results are obtained in general on the daily administration of from 0.3 to 100 milligrams per kilogram of body weight, preferably given in divided doses 2 to 4 times a day, or in sustained release form. For most mammals the administration of from 20 to 1500 milligrams per day provides satisfactory results and dosage forms suitable for internal administration comprise 5 to 950 milligrams of the compound in admixture with a solid or liquid pharmaceutical carrier or diluent.

For the use indicated above, the compounds may be combined with a pharmaceutically acceptable carrier, and such other conventional adjuvants as may be necessary, and administered orally or parenterally. For most uses, oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phophate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for prophylatic treatment of bronchial asthma and prepared by conventional tabletting techniques to contain the following ingredients:

| Ingredients | Weight (mg.) |
| --- | --- |
| 10-(2-thienylmethyl)-2,3-dihydro-imidazo[2,1-b]quinazolin-5(10H)-one | 25 |
| Tragacanth | 10 |
| Lactose | 222.5 |
| Corn Starch | 25 |
| Talcum | 15 |
| Magnesium Stearate | 2.5 |

A representative formulation is also a capsule for oral administration 2 to 4 times a day for prophylatic treatment of bronchial asthma and prepared by conventional capsulating techniques to contain the following ingredients:

| Capsule Ingredients | Weight (Mg.) |
| --- | --- |
| 10-(2-thienylmethyl)-2,3-dihydro-imidazo[2,1-b]quinazolin-5(1oH)-one | 10 |
| Lactose | 316 |
| Sterotex K (a triglycerol ester lubricant) | 10 |

In addition the compounds of the formula I may be administered as bronchodilators by inhalation therapy in a conventional manner, e.g., by the use of nebulizers, vaporizers, aerosols and the like. Compositions for use in administration by inhalation therapy may be prepared accordingly to conventional procedures and contain the usual conventional ingredients employed in such compositions. A representative aerosol formulation prepared by conventional techniques for use with a metered value system contains the following ingredients:

| | |
| --- | --- |
| 10-(2-thienylmethyl)-2,3-dihydro-imidazo[2,1-b]quinazoline-5(10H)-one | 0.4 – 20% |
| Ethyl alcohol | 10 – 40% |
| Ascorbic acid | 1 – 10% |
| Freon 11 | 10 – 30% |
| Freon 114 | 10 – 30% |
| Freon 12 | 30 – 60% |
| Buffer System - pH control | q.s. |
| Flavor | q.s. |

The following examples show representative compounds encompassed within the scope of this invention and the manner in which such compounds are prepared. However, it is to be understood that the examples are for purposes of illustration only.

EXAMPLE A

N-(furfuryl)isatoic anhydride

Step A: To a mixture of 50 g. of 2-furylmethanol, 50 ml. of pyridine and 50 ml. of diethyl ether cooled to minus 10°C. is added dropwise a solution of 41 ml. of thionyl chloride in 50 ml. of diethyl ether. After addition the reaction mixture is extracted 3 times with diethyl ether. The extracts are combined and evaporated to an oil which is distilled at 40°C. and 16 mm/Hg. to obtain 2-(chloromethyl)furane.

Step B: To a solution of 30 g. of isatoic anhydride in 300 ml. of dimethylacetamide is added 9.0 g. of pentane washed sodium hydride. After stirring for 1 hour at room temperature, 25 g. of 2-(chloromethyl)furane is added and the mixture stirred for 5 hours at room temperature. The resulting mixture is evaporated to one third its volume, cooled and poured over 500 ml. of ice water. The resulting precipitate is recovered by filtering, washed with water, dried under reduced pressure, dissolved in 500 ml. of methylene chloride, treated with sodium bicarbonate solution, alumina and charcoal, dried and filtered through celite. The methylene chloride is exchanged for diethyl ether and the resulting precipitate is recovered by filtering, washed with dimethyl ether and dried under reduced pressure to obtain N-(furfuryl) isatoic anhydride, m.p. 131°–133°C.

EXAMPLE B

N-(2-thienylmethyl)isatoic anhydride

Step A: A mixture of 105 g. of thiophene and 50 ml. of hydrochloric acid is cooled with vigorous stirring to minus 10°C. and there is then added dropwise 125 ml. of 37% aqueous formaldehyde solution while maintaining the temp. below plus 10°C. There is added 100 ml. water and the mixture extracted 3 times each with 125 ml. of diethyl ether. The extracts are combined, washed twice with sodium bicarbonate and then twice with water, dried, evaporated and the resulting oil distilled at 70°C. and 12 mm/Hg. to obtain 2-(chloromethyl)-thiopene.

Step B: Following the procedure of Step B of Example A but employing 2-(chloromethyl)-thiopene in place of 2-(chloromethyl)-furane there is obtained N-(2-thienylmethyl) isatoic anhydride, m.p. 137°–140°C.

EXAMPLE 1

10-(2-thienylmethyl)-2,3-dihydro-imidazo[2,1-b]quinazolin-5(10H)-one.

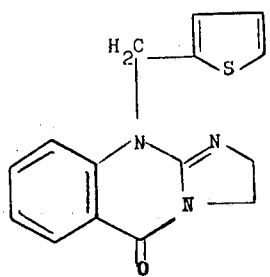

A mixture of 20 g. of N-(2-thienylmethyl)isatoic anhydride, 9 g. of 2-methylmercapto-imidazoline and 1 pellet of potassium hydroxide in about 300 ml. of dioxane is heated at reflux for 5 hours, the solvent then evaporated off and the residue dissolved in methylene chloride. After washing twice with water the solution is extracted 3 times with 1N. hydrochloric solution. Heating on a steam bath avoids precipitation and after filtering hot through celite, sodium bicarbonate solution is added and the resulting precipitate is recovered by filtering, washed with water, dissolved in methylene chloride and the methylene chloride exchanged for diethyl ether. The resulting precipitate is recovered by filtering, washed with diethyl ether and dried under reduced pressure at 40°C. to obtain 10-(2-thienylmethyl)-2,3-dihydro-imidazo[2,1-b]quinazolin-5(10H)-one, m.p. 124°–127°C.

EXAMPLE 2

Following the procedure of Example 1 the following compounds of the invention are obtained:

a. 10-furfuryl-2,3-dihydro-imidazo[2,1-b]quinazolin-5(10H)-one, m.p. 150°–153°C.

b. 10-(2-thienylmethyl)-7-chloro-2,3-dihydro-imidazo [2,1-b]quinazolin-5(10H)-one.

c. 10-(2-thienylmethyl)-2-methyl-2,3-dihydro-imidazo [2,1-b]quinazolin-5(10H)-one.

d. 11-(2-thienylmethyl)-2,3,4,11-tetrahydropyrimido [2,1-b]quinazolin-6-one.

e. 12-(2-thienylmethyl)-2,3,4,5-tetrahydro-(12H)-diazepino[2,1-b]quinazolin-7-one.

f. 10-[2-(4'-chloro)thienylmethyl]-2,3-dihydroimidazo[2,1-b]quinazolin-5(10H)-one.

g. 10-(2-thienylmethyl)-3-methyl-3-ethyl-2,3-dihydroimidazo[2,1-b]quinazolin-5(10H)-one.

What is claimed is:

1. A compound of the formula:

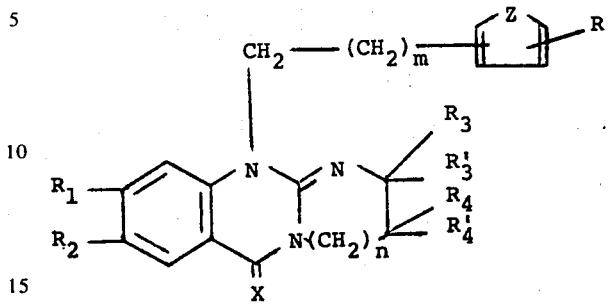

wherein
each of $R_1$ and $R_2$ is, independently, hydrogen, halo of atomic weight not greater than 36 or alkyl of 1 to 3 carbon atoms, or both are alkoxy of 1 to 2 carbon atoms; or one is hydrogen and the other bromo or alkoxy of 1 to 2 carbon atoms, $n$ is 0, 1 or 2, $m$ is 0, 1 or 2, Z is oxygen or sulfur, X is oxygen or sulfur, R is hydrogen, halo of atomic weight of 18 to 36 or alkyl of 1 to 4 carbon atoms, and each of $R_3$, $R_3'$, $R_4$ and $R_4'$ is hydrogen or alkyl of 1 to 3 carbon atoms provided that no more than 3 of $R_3$, $R_3'$, $R_4$ and $R_4'$ are alkyl, or a pharmaceutically acceptable acid addition salt thereof.

2. A compound of claim 1 in which X is oxygen.

3. A compound of claim 2 in which each of $R_1$ and $R_2$ is hydrogen.

4. A compound of claim 2 in which each of $R_1$, $R_3$, $R_3'$, $R_4$ and $R_4'$ is hydrogen.

5. A compound of claim 1 in which Z is oxygen.

6. A compound of claim 1 in which Z is sulfur.

7. The compound of claim 6 which is 10-(2-thienylmethyl)-2,3-dihydro-imidazo[2,1-b]quinazolin-5(10)-one.

* * * * *